United States Patent
Bongardt et al.

[11] Patent Number: 5,887,077
[45] Date of Patent: *Mar. 23, 1999

[54] METHOD FOR THE RECOGNITION AND EVALUATION OF DEFECTS IN REFLECTIVE SURFACE COATINGS

[75] Inventors: Wolfgang Bongardt, Würselen; Martin Lorek, Düren; Ekkehard Wilde, Bergisch Gladbach, all of Germany

[73] Assignee: Saint-Gobain Vitrage, Courbevoie, France

[ * ] Notice: This patent issued on a continued prosecution application filed under 37 CFR 1.53(d), and is subject to the twenty year patent term provisions of 35 U.S.C. 154(a)(2).

[21] Appl. No.: 614,606

[22] Filed: Mar. 13, 1996

[30] Foreign Application Priority Data

Mar. 15, 1995 [DE] Germany .......................... 195 09 345.3
Aug. 18, 1995 [EP] European Pat. Off. ........... 95401909.7

[51] Int. Cl.⁶ ........................................... G06K 9/46
[52] U.S. Cl. ........................................ 382/149; 382/165
[58] Field of Search ................................... 382/108, 141, 382/149, 165; 348/234; 358/520

[56] References Cited

U.S. PATENT DOCUMENTS

| | | | |
|---|---|---|---|
| 4,812,904 | 3/1989 | Maring et al. | 382/165 |
| 5,073,952 | 12/1991 | Watanabe | 382/216 |
| 5,225,890 | 7/1993 | Lee et al. | 356/371 |
| 5,317,648 | 5/1994 | Sawada et al. | 382/17 |
| 5,335,293 | 8/1994 | Vannelli et al. | 382/17 |
| 5,377,277 | 12/1994 | Hansafusa et al. | 382/141 |
| 5,392,359 | 2/1995 | Futamura et al. | 382/141 |
| 5,396,080 | 3/1995 | Hannotiau et al. | 250/560 |

FOREIGN PATENT DOCUMENTS

| | | | |
|---|---|---|---|
| 23 18 532 | 11/1973 | Germany . | |
| 2318532 | 11/1973 | Germany . | |
| 43 09 802 | 9/1994 | Germany | G01J 3/46 |
| 2 270 561 | 3/1994 | United Kingdom | G01J 3/50 |

OTHER PUBLICATIONS

Patent Abstract of Japan, vol. 018, No. 162 (P–1712), 17 Mar. 1994 & JP 05 332838A (Imaizumi Shokai:KK), 17 Dec. 1993.

*Primary Examiner*—Jose L. Couso
*Assistant Examiner*—Matthew C. Bella
*Attorney, Agent, or Firm*—Pennie & Edmonds LLP

[57] ABSTRACT

The recognition and evaluation of locally limited colour defects in a reflective surface coating on a glass plate are carried out by digital data processing of an image delivered by a colour video camera. To this end, the coated glass plate (1) is illuminated using white light, and the light reflected by the surface coating (3) is made visible on a projection screen (6). The image appearing on the projection screen (6) is acquired by one or more colour video cameras (12, 13, 14, 15). For each of the three primary colours of the surface acquired by the colour video camera, the luminance is determined for each pixel. The relative colour fraction is determined by dividing the determined luminance values of each primary colour by the sum of the luminance values of the three primary colours at the corresponding pixels. The relative colour fractions are compared with predetermined set values.

19 Claims, 6 Drawing Sheets

METHOD FOR THE RECOGNITION AND EVALUATION OF DEFECTS IN REFLECTIVE SURFACE COATINGS

DESCRIPTION

The invention relates to a method for the recognition and evaluation of locally limited defects in a surface coating on a substrate by digital data processing of an image delivered by a video camera.

Glass plates, hereafter referred to as "panes", which have a selectively reflective surface coat are used as sun-protection glazing and/or thermally insulating glazing. Selectively reflective coatings can be applied using various methods. Such coatings are currently applied on an industrial scale by the method of cathodic sputtering sustained by a magnetic field. In this case, a thin silver layer, which is inserted between other layers, usually acts as the functional coating proper. Such a layered structure generally comprises a metal oxide adhesive layer, a silver layer inserted between protective metallic layers and a metal oxide cover layer.

In a related technical field, various methods are known for manufacturing mirrors on a substrate. Whether in the case of "front-face" mirrors, where the reflection takes place on the coating without the light passing through the substrate or, in the case of transparent substrates, with traditional mirrors, these mirrors can benefit from the techniques of the invention.

Local coating defects of various types and of variable extent can occur in all coating processes. When the substrate is transparent, such defects can often not be recognized by transparency through the coated pane, but can be noticed mainly in reflection, because they cause, for example, locally limited colour changes. Since, when they have been installed, coated panes can always be seen in reflection, such coating defects should also be recognized and panes with a defective coating should be eliminated. To date, this has been done exclusively by visual assessment because satisfactory automatic methods have not hitherto existed.

It is accepted that, when coatings are applied using the cathodic sputtering method, disturbances in the coating process during application of the metal oxide coatings give rise to such local defects. In particular, in the case of a high sputtering rate, electrically insulating metal oxide deposit layers can form, especially on the lateral anodic surfaces inside the sputtering chambers, and these cause the appearance of electrical discharges from this target surface to the lateral anodic surfaces. A particularly intense plasma is thus formed locally and creates the mentioned coating defects in the form of spots. Similarly, in the techniques of manufacturing coatings by pyrolysis or by CVD, point-like defects created, for example, by a drop of liquid falling onto the substrate, or by a "pinhole" deposition gap at a specific position as a result of the presence of a foreign particle, are common.

The object of the invention is to provide an automatic method which can reliably recognize any type of spot-like coating defect and evaluate them using the objective criteria. The method should allow reliable assessment of the reflective coatings and should be suitable for an industrial application.

According to the invention, this object is achieved in that the coated substrate is illuminated with wide-band light in the visible spectral range, preferably with white light, and a colour video camera is used as the video camera, and in that the digital data processing is carried out by detecting, for each pixel, the luminance values for each of the three primary colours and by determining, by dividing the luminance values of each primary colour by the sum of the luminance values of the three primary colours, the relative colour fraction for each primary colour in each pixel, then by comparing the relative colour fractions with predetermined set values.

The invention also provides for the suitable use of digital data processing in the case of a video measurement system for assessing a purely reflective, or selectively reflective and transparent, surface coating, for which stringent requirements regarding the uniformity of the colours in transmission, and particularly in reflection, are set.

It is indeed fundamentally known, with the aid of digital data processing in the case of a video measurement system including a processor, to evaluate metrologically the image signals delivered by the television camera, and in this way to detect both irregular surfaces and differences in luminosity and colour values (Messen+Prüfen/Automatik January/February 1977, pages 34–41). However, it has become apparent that determining the colours by image analysis using a colour video camera and assessing coating defects in spot form in partially reflective large-area surface coatings by using this fundamentally known method leads to usable results only if the method according to the invention has first been used to calculate for each pixel, from the measured luminance values of three primary colours, the ratio of the measured luminance value of each primary colour to the sum of the luminance values of all the primary colours at this pixel, and if the relative colour fraction thus determined is used as the basis for the subsequent evaluation. In particular, this eliminates local differences in the illumination intensity, which are unavoidable in the case of large-area coated substrates and which have an inevitable effect on the luminance values measured. The relative colour fractions thus obtained are also independent of local variations and local and/or temporary fluctuations in the illumination intensity and allow a highly sensitive assessment of the colour, even in the case of variable and/or irregular illumination. It is, however, assumed that, at all places on the coating to be examined, the light striking the surface coating to be assessed has, in the visible spectral range, the same mixture of the various wavelengths contained in the light spectrum, so that the illumination alone cannot give rise to the fact that different relative colour fractions of the three primary colours are measured.

When there is the risk that the lighting installation used cannot illuminate the surface coating over the entire surface to be assessed with a locally constant distribution of the colour fractions, provision is made in a development of the invention to first determine, for the entire surface to be assessed, the relative colour fractions which depend on the position on a substrate having a defect-free surface coat and to store the values thus determined as reference values, then, in the case of identical illumination, to divide the relative colour fractions which depend on the determined position on the coated substrate to be studied by the reference values which depend on the stored position. In this way, it is then possible to eliminate not only different illumination intensities on the surface to be assessed, but also different spectral distributions in the illumination.

Since particularly weak colour spots in surface coatings of glass plates constitute less of a problem in transparency than in reflection, the method according to the invention is preferably used for evaluating reflected light. In this case, it is advantageous to illuminate the coated glass pane on the coated side and to detect the light reflected by the interface between the air and the surface coating by using a colour camera. It is, however, also possible to illuminate the coated glass plate on the surface opposite the coating and to detect the light reflected by the interface between the glass and the surface coating or between the surface coating and the air, through the glass plate.

Basically, the colour video camera detects and evaluates the diffuse-reflection image from the surface coating. The diffuse-reflection image can be generated in various ways. Thus, it is possible according to a first embodiment to illuminate the surface coating by light directed at an oblique angle of incidence and to make the reflected light visible on a projection screen as diffusely reflected light, with the colour video camera detecting the image visible on the projection screen. According to another embodiment, the diffusely reflected light is detected by the colour video camera directly from the surface coating or from the substrate, when the surface coating is illuminated by diffuse light. Illumination of the surface coating by diffuse light is done in various ways using known means.

When the colour video camera is directed directly at the surface coating or at the coated substrate, care should be taken that the fraction of light rays which are not directly attributable to the light reflected from the surface coating is as small as possible. This can be obtained by observing the coated substrate on a light-absorbing background, for example on a black background.

Depending on the size of the surface to be assessed, one or more colour video cameras may be used. In the case of assessing a small surface, for example a small coated glass plate, the entire surface can be acquired at once using a single camera. However, when the method is used, for example, at the end of a coating installation for large glass plates, for example for float glass plates with length 6 m and width approximately 3 m, the measurement is expediently taken by simultaneously using a plurality of colour video cameras. According to a preferred embodiment, a narrow evaluation band extending over the entire width of the glass plate is observed and evaluated at short short successive distances with the aid of a plurality of colour video cameras. In this way, the luminance profiles of the three primary colours over short distances can be established and evaluated over the entire width of the glass plate, for example, with a fixed arrangement of the video cameras above a roll conveyor conveying the glass plate, and with the coated glass plate advancing continuously. When the mutual separation of the successive evaluation bands and the luminance profiles determined for these evaluation bands is, for example, a few centimeters, the entire surface of the glass plate can be studied using this method with an accuracy which is satisfactory as regards the colour defects mentioned.

During evaluation and digital processing of the signals delivered by the colour video camera itself, or by an image processing stage placed after the colour video camera proper, for the luminance values of the three primary colours using the method according to the invention, known processing and optimization methods may be resorted to. The colour signal delivered by the video camera is usually decomposed into the three primary colours (red, green and blue) independently of the corresponding camera type. The intensity of these primary colours, that is to say the luminance value of each primary colour, is then available for subsequent processing in three separate image memories for each pixel.

However, before determining the relative colour fraction, filtering and optimization measures are expediently taken in order to obtain optimum evaluation of the measured values.

The optimization measures comprise, in particular, a transformation of the luminance values, that is to say of the intensity values, advantageously in such a way that the observed intensity interval of each primary colour is extended to the entire available intensity range of the associated image memory. Such a transformation permits optimal assessment of the colour contrast or of existing colour gradations. An intensity transformation can be performed, for example, in the form of a linear transformation of the intensity interval, between the lowest value and the highest value of luminance or intensity measured, onto the entire available intensity range of the associated image memory. Similarly, it is also possible to perform an intensity transformation according to the method termed "histogram equation". This transformation is expediently undertaken directly using the video signal itself, that is to say before digitization and storage of each luminance value in each associated image memory.

The filtering measures serve, in a manner known per se, on the one hand for parasite elimination, that is to say for increasing the useful-signal/noise ratio, and on the other hand for averaging and smoothing the signals. In the case of filtering for parasite elimination, the most favourable compromise should be sought between undesired distortion and effective parasite elimination from the original signal. Since the case in question is that of assessing colour defects with a relatively large extent, averaging operations are effective and satisfactory for the signals present.

When optimization and filtering measures are taken before determining the relative colour fractions, it is in principle possible to adopt a procedure whereby the intensity transformation is performed first and the signals obtained after the transformation are subjected to averaging and parasite elimination by two-dimensional local filtering. It is, however, also possible to filter the signals delivered by the colour video camera or by the image processing stage following the colour video camera first of all, in a local two-dimensional filtering step, and then to transform the filtered signals and to process them further.

After the relative colour fraction in each pixel and therefore the local colour distribution in the measurement field have been determined for the three primary colours from the transformed and filtered signals, it is simply necessary to compare the values determined with a defined standard value. When there are colour abnormalities, this may, for example, be done by comparing the relative colour fraction determined with a set value which corresponds to the relative colour fraction in the surrounding medium when in the absence of defects. On the other hand, when there is an inhomogeneous colour distribution in the illumination because of the nature of the lighting installation, it is suitable, as already mentioned above, to determine and store the local colour distribution of the diffusely reflected image from a defect-free surface, and to use the stored values of the relative colour fractions as set values for the comparison between the set value and the actual value.

Particular features and additional advantages of the invention will emerge from the claims and the following description of various embodiments, which is based on the drawings.

Figure 1:
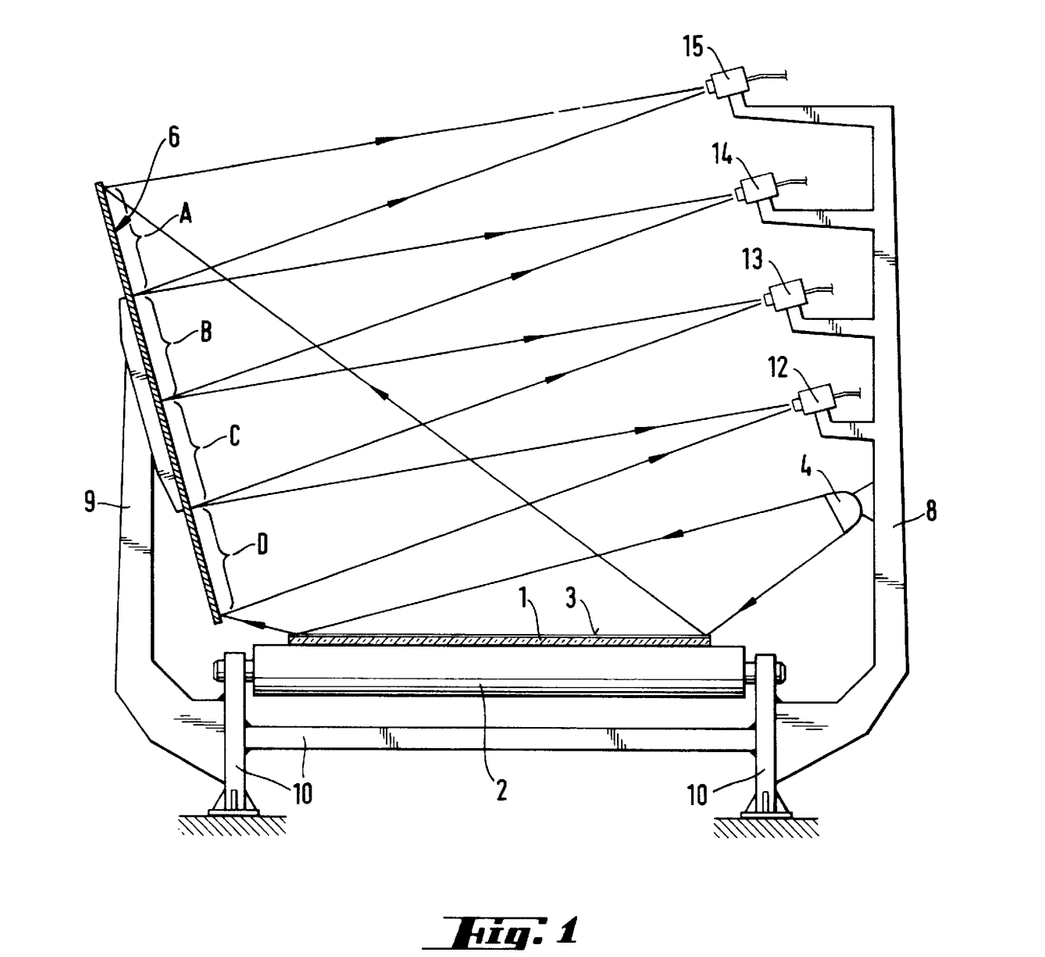
FIG. 1 shows a suitable set-up for implementing the method, including measurement by indirect reflection.

The glass plate 1 represented in FIG. 1 is, for example, a 4 m thick float glass plate having a width of approximately 3.2 m and a length of 6 m, which is conveyed in the horizontal position on conveyor rolls 2. The glass plate 1 is provided on its upper face with a coating 3 which reflects thermal radiation and has already been applied using the method of cathodic sputtering sustained by a magnetic field. For illumination of the coated glass plate 1, use is made of a light projector 4 which is arranged laterally above the plane of the glass plate and is used to project directed white light at an oblique angle of incidence onto the coating 3. Although the angle of incidence of the light rays unavoidably increases as the distance of the illuminated zone from the projector increases, this change in the angle of incidence does not significantly affect the measurement so long as the angle of incidence of the radiation does not exceed approximately 70°. The geometrical deformations due to the variable angle of incidence can be compensated for by calculation.

The white light from the light projector 4 is reflected by the partially reflective coating at an angle of reflection corresponding to the angle of incidence. The reflected light rays are visualized on a plane projection screen having a dispersive white surface. Where local coating defects are present at corresponding positions on the coating 3, visible coloured spots appear on the projection screen 6, and the surface dimensions of these spots correspond, if appropriate after taking into account geometrical deformations, to the dimensions of the coating defects. The projector 4 and the projection screen 6 are suitably mounted by means of fastening uprights 8 or 9 on the frame 10 of the roll conveyor, or are fixed in place in a different way.

Four colour video cameras 12, 13, 14 and 15 are mounted one above the other using suitable fixtures on the fastening upright 8 above the light projector 4. These colour video cameras 12 to 15 are each equipped with a suitable objective lens and have their optical axis directed perpendicularly to the projection screen 6, so that each video camera acquires one quarter of the total height of the image appearing on the projection screen 6, with the four acquired fields overlapping or being juxtaposed with one another. In this way, the light rays reflected by the coating 3 are acquired on the projection screen 6 over the entire width of the glass plate 1.

The colour video cameras 12 to 15 are installed identically. An image processing system is connected to each video camera, this system being represented with its essential components in the form of a block diagram in FIG. 2. The colour video image processing system comprises the colour video camera 12 (13, 14, 15) and, in each case, one colour video digitalization stage controlled by each colour video camera. For each of the three primary colours, it contains a matrix image memory 16, 17, 18. For each pixel, each image memory, 16, 17, 18 stores the digital luminance value of the primary colour corresponding to the respective pixel in the field of view of the camera. In order to make it possible to describe the luminance of the three primary colours with sufficient accuracy, the overall luminosity range to be detected should be subdivided into a sufficiently large number of luminance levels. The number of luminance levels should be at least 64, and good results are obtained when, for example, 256 luminosity or luminance levels are available for describing the luminance of each pixel taken individually.

Figure 2:
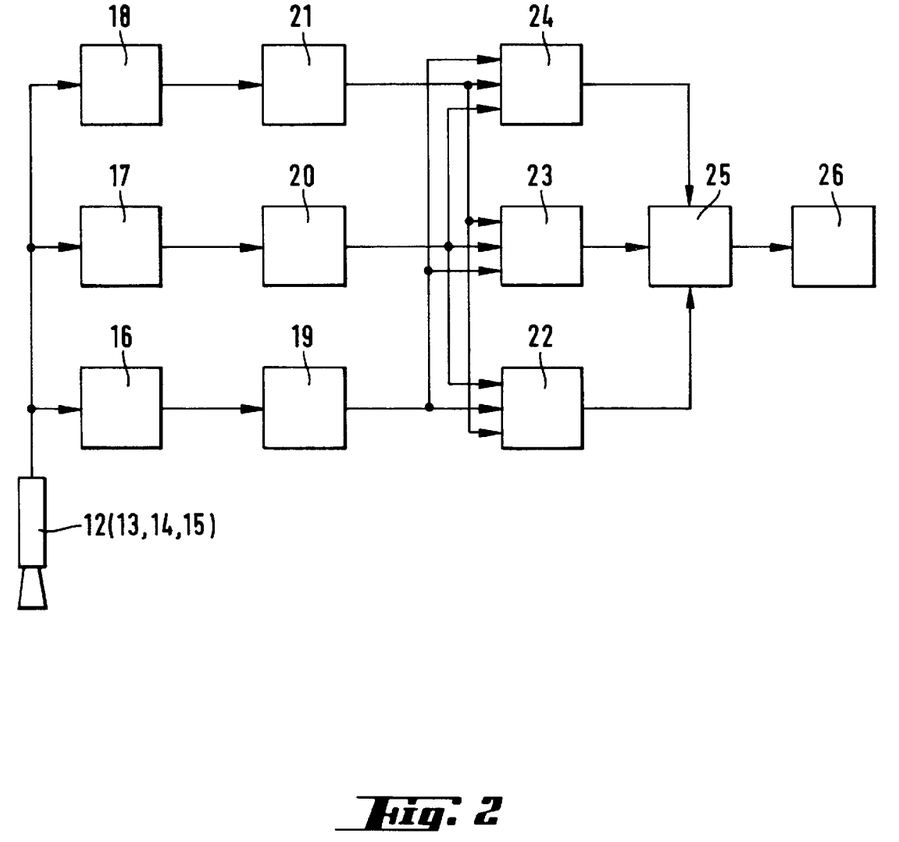
FIG. 2 is a block diagram of a circuit intended for evaluating the luminance signals delivered by a colour video camera.

In the case of the representation chosen here, each colour video camera is provided with its own image processing system. It is, however, possible to use instead a high-efficiency image processing system which can simultaneously process the signals delivered by all the colour video cameras. The processing of the signals themselves nevertheless remains fundamentally identical.

As shown by the block diagram in FIG. 2, an optimization and filtering stage 19, 20, 21 is controlled by the image memories 16, 17 and 18 which each deliver the original luminance signals of a defined field. The purpose of these optimization and filtering stages 19, 20, 21 is to carry out an intensity transformation of the luminance signals and a two-dimensional local filtering of the signals, in order to eliminate parasites and to smooth the signals and to deliver a mean value representative of the luminance of a colour in a chosen field. The filtering and signal processing techniques required for this are known and therefore need not be described in detail. Whereas the filtering and optimization stage 19 delivers the luminance profile, for example, of the colour red, which is composed of the processed signals from the entire observed image width, the filtering and optimization stage 20 delivers the luminance profile, for example, for the colour green and the filtering and optimization stage 21 delivers the luminance profile, for example, for the colour blue.

The signals delivered by the filtering and optimization stages 19, 20, 21 are fed to the division stages 22, 23, 24, with the signals of the three primary colours being delivered to each division stage. In these division stages 22, 23, 24 the luminance values of the three primary colours are compared with the corresponding total luminosity, that is to say with the sum of the luminance values of the three primary colours. After the division performed at this point, the signal of the relative colour fraction of the corresponding primary colour appears at the output of the division stage 22, 23, 24 in question.

The signals appearing at the output of the division stages 22, 23, 24 are then fed to a colour comparison stage 25. In this colour comparison stage 25 the colours of each primary colour at each position on the image are compared with a predetermined set value, with the relative colour difference for each primary colour being in each case calculated from the set values and the actual values for the relative colour fractions.

The difference signals obtained by the colour comparison at the output of the colour comparison stage 25 are subsequently sent to an evaluation stage 26. The allowed limit values, which were determined beforehand on the basis of visual assessments, are introduced in this evaluation stage 26. Preferably, for each primary colour a lower limit value and an upper limit value are introduced in this case for the difference signals (that is to say for the difference between the set value signal and the actual value signal), which cannot be exceeded or fallen below. However, it is also possible instead to take the sum of the absolute values of the difference signals of the relative colour fractions of the three primary colours and to compare this sum signal with an upper limit value which cannot be exceeded. When the limit values introduced are exceeded or fallen below, the evaluation stage 26 delivers a corresponding signal, so that defective coatings can thereby be recognized and, if appropriate, eliminated.

Figure 3:
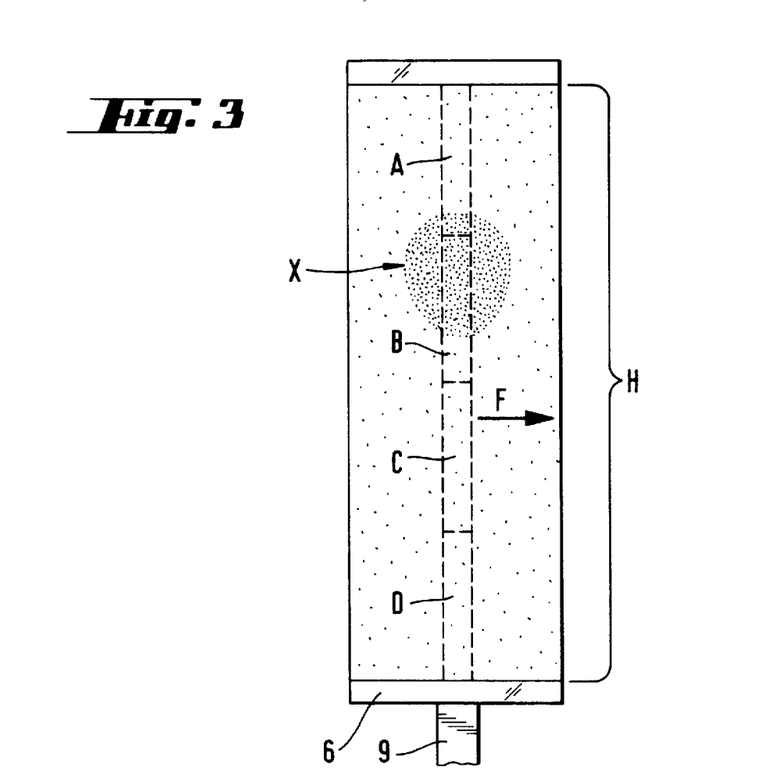
FIG. 3 shows the narrow measurement field acquired by the colour video cameras, in the case of the set-up according to FIG. 1, from the projection screen.
Figure 4:
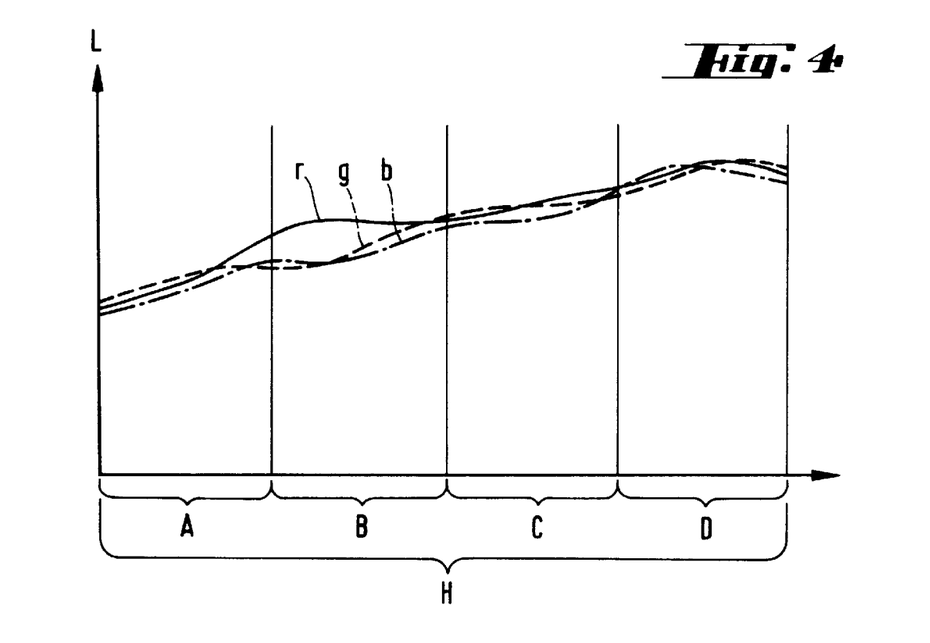
FIG. 4 shows a graphical representation of the luminance profiles of the three primary colours which are obtained over the width of the glass plate after processing the digital signals.

FIG. 3 once more illustrates the mode of operation of the method, while FIG. 4 shows one possibility for representing the measurement results. While the glass plate moves, for example, in the horizontal position on a roll conveyor (FIG. 1), the reflection image produced by the coating 3 in a zone between two conveyor rolls moves in the direction of the arrow F on the projection screen 6, which may have a comparatively small width dimension in the direction of movement of the glass plate. The four video cameras acquire from the projection screen 6 a narrow evaluation band extending over the entire height H of the projected image and subdivided into four zones A, B, C and D which are assigned to the individual colour video cameras. Evaluation is carried out by recording the measurement fields simultaneously using four colour video cameras with a short exposure time at short time intervals. The recorded image is stored in each image processing system and is evaluated as described with reference to FIG. 2. When the glass plate has advanced by a few centimeters, the next photographs are taken simultaneously with the four colour video cameras, together with storage and subsequent evaluation of the video images. In this way, the entire glass plate can be acquired and evaluated in successive transverse bands.

If matrix cameras are being used, the range photographically acquired in the direction of movement of the glass plate may have a value of up to 160 cm. During the image processing, it can then be subdivided into evaluation bands, a few centimeters wide and extending in the transverse direction, and be evaluated in the manner described. If linear cameras are being used instead of matrix cameras the photographs should be taken at distances of a few millimeters in order to make it possible to carry out the required local filtering in the form of evaluation bands.

If the luminance value L, obtained when photographing with four colour video cameras, is plotted after processing the video signals for the three primary colours against the width H of the glass plate, a diagram as represented in FIG. 4 is obtained. So long as the reflected light acquired by the colour video cameras is white, or neutral as regards colour, the three luminance curves r (red), g (green) and b (blue) have profiles which are nearly parallel to each other or, in the ideal case, are superimposed. The absolute height of the luminance curves, under practical illumination conditions, is not constant since the luminance on the projection screen is, in the case of the set-up described here, in fact much less in the field A because the coated glass plate is further away, and it increases continuously to the end of the field D.

This change in the luminance of the white light does not affect the evaluation. Only the fact that the variations in the relative colour fractions are recognized is important here. In the example represented, in which the projection image has a slightly red-coloured spot in the zone X, the luminance curve r for the colour red increases markedly in the corresponding fields A and B, whereas the luminance curves g, for green, and b, for blue, decrease slightly. The colour fraction of the primary colour red therefore increases, whereas the colour fraction of the primary colours green and blue decreases. When the set values for the relative colour fractions are calibrated and adjusted accordingly, clear information regarding the quality of the coat can be obtained.

Figure 5:
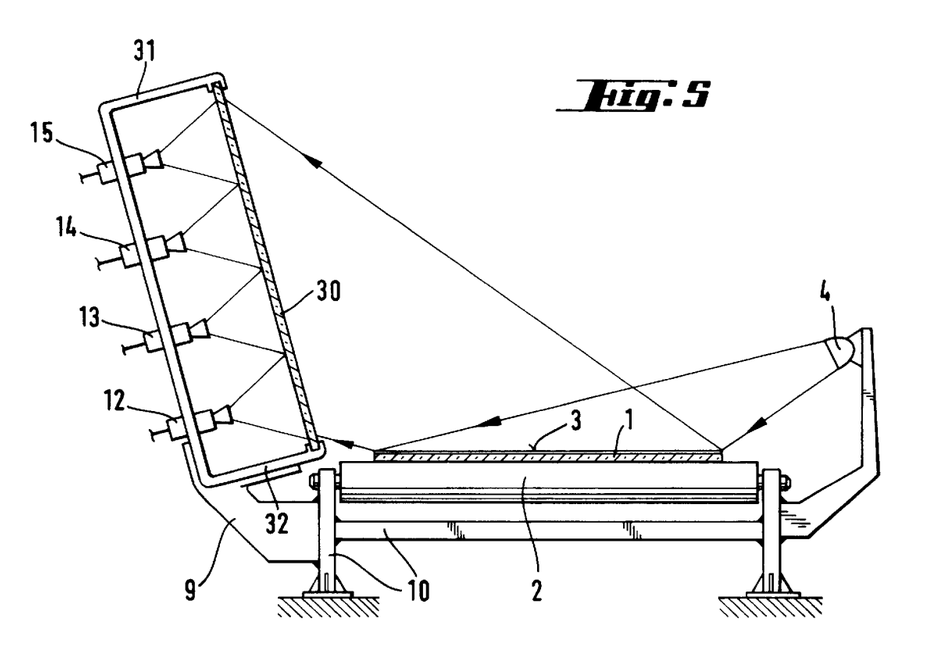
FIG. 5 shows another set-up for implementing the method including measurement by indirect reflection.

Another embodiment, for an indirect-reflection measurement set-up, is represented in FIG. 5. Once again, colour defects are being evaluated in a transparent surface coating 3 on a large glass plate 1 which passes through a measurement field transverse to the direction of advance of the glass plate 1 on the conveyor rolls 2 of a roll conveyor. Here again, the surface coating 3 in the measurement field is illuminated using a directional projector 4 which directs the light rays obliquely onto the surface coating at angles of between 40° and 60° with respect to the normal. The light rays reflected at the surface coating strike the projection screen which, in this case, consists of a dispersive pane 30, for example a pane of opal or opaque glass. The dispersive pane 30 is fixed by uprights 31, 32 to a support 9 which is mounted on the frame 10 of the roll conveyor. Inside the opal pane 30, the light rays striking the opal pane 30 are dispersed in all directions, so that the diffusely radiating representation of the reflected image can be acquired from the rear of the opal pane 30 using the colour video cameras 12 to 15. The signals delivered by the colour video cameras 12 to 15 are digitally processed in the same way as described with reference to FIGS. 1 to 4.

Figure 6:
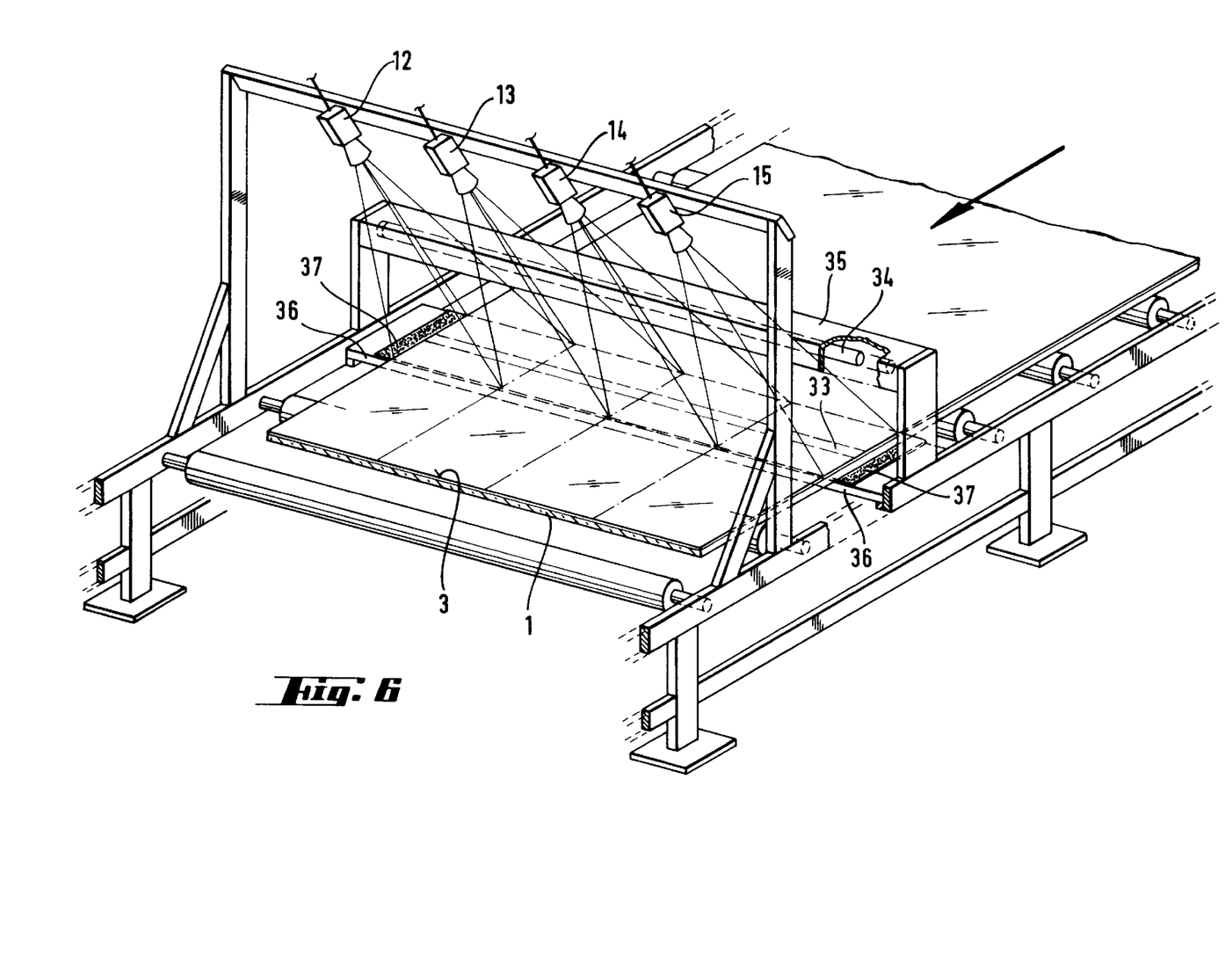
FIG. 6 shows a set-up for implementing the method in the case of measurement by direct reflection.
Figure 7:
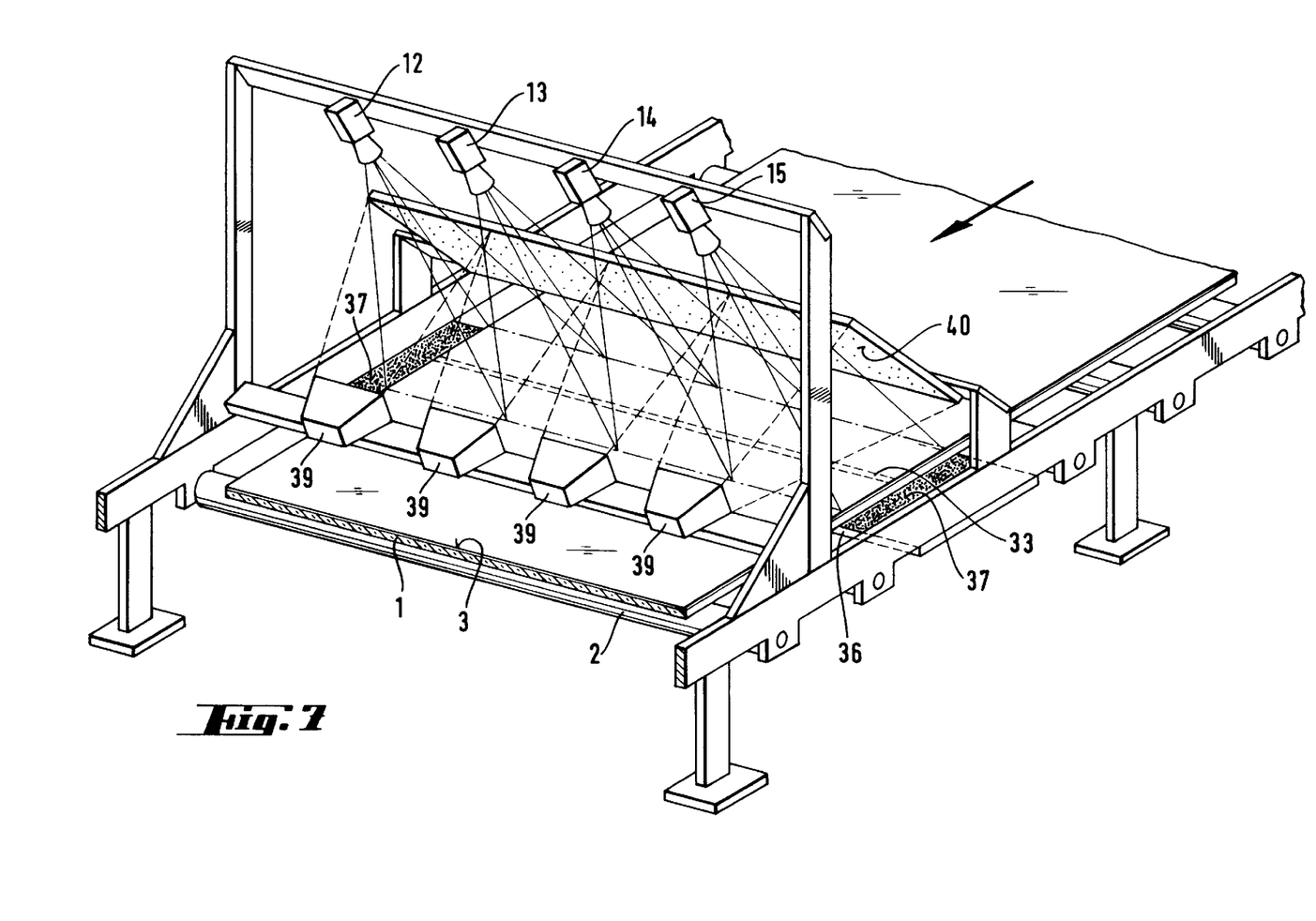
FIG. 7 shows another set-up for implementing the method in the case of measurement by direct reflection.

FIGS. 6 and 7 show two illustrative embodiments for direct-reflection measurements, that is to say for direct detection and evaluation of the colour image appearing on the surface coating, with illumination of the surface coating under diffuse light, the difference between these two illustrative embodiments being the type of illumination. Both cases again relate to a float glass plate 1, provided with a partially reflective surface coating 3, which is transported on conveyor rolls 2 and is examined during transport in order to detect colour defects in the surface coating. Between two successive conveyor rolls 2, transversely to the direction of transport of the glass plate, four colour video cameras 12, 13, 14, 15 are mounted above the roll conveyor on a suitable support. With the aid of these cameras, a field extending over the entire width is once again acquired and, inside this field, a narrow evaluation band 33 with a width of, for example, approximately 3 cm, is evaluated. The signals delivered by the colour video cameras 12 to 15 for the three primary colours is again evaluated according to the method described.

In the case of the embodiment represented in FIG. 6, the diffuse illumination is carried out using fluorescent tube 34 which is arranged above the glass late 1, parallel thereto and transversely to the direction of transport of the glass pane. The fluorescent tube 34 is protected at the top by a casing 35. The diffuse light thus obtained strikes the surface coating 3 directly and produces a luminous band extending transversely over the glass plate. In order to prevent the light passing through the surface coating 3 and the glass plate 1, which is reflected below the glass plate and which passes back to the glass plate 1 and the coating 3, from being superposed on the reflection image appearing on the surface coating 3, a plate 36 whose surface is provided with a light-absorbing black coat 37 is arranged below the glass plate 1 in the measurement field zone.

In the case of the set-up illustrated in FIG. 7 as well, a plate 36 having a light-absorbing black coat 37 is arranged below the glass plate 1 in the measurement field zone, in order to prevent superposition of the reflection image from the surface coating 3 with the reflection of light below the glass plate 1. The diffuse illumination of the surface coating 3 is in this case carried out indirectly with the aid of projectors 39 which are directed at a dispersion wall 40, preferably arranged inclined above the glass plate, transversely to the transport direction. The dispersion wall 40 has a white dispersive surface, so that diffuse light is reflected by this dispersive wall. That fraction of this diffuse light which strikes the surface coating 3 diffusely illuminates the coating and once again allows indirect observation of the coating by the colour video cameras.

We claim:

1. Method for the recognition and evaluation of locally limited defects in a surface coating on a substrate by digital data processing of an image delivered by a video camera, characterized in that the coated substrate is illuminated with wide-band light in the visible spectral range, preferably with white light, and a colour video camera is used as the video camera, and in that the digital data processing is carried out by detecting, for each pixel, the luminance values for each of the three primary colours and by determining, by dividing the luminance values of each primary colour by the sum of the luminance values of the three primary colours, the relative colour fraction for each primary colour in each pixel, then by comparing the relative colour fractions with predetermined set values.

2. Method according to claim 1, characterized in that in the case of illuminating the surface coating to be assessed with a locally constant distribution of the colour fractions in the light, the relative colour fractions determined are directly compared with the reference set values which are constant over the area of the surface coating.

3. Method according to claim 1, characterized in that, in the case of illuminating the surface coating to be assessed with a locally varying colour fraction distribution in the light, the relative colour fractions dependent on the position on a substrate having a defect-free surface coat are determined and stored, and in that the position-dependent relative colour fractions determined for the surface coating to be assessed are compared with the position-dependent relative colour fractions stored as reference set values.

4. Method according to claim 1, characterized in that the light reflected from the surface coating is recorded and evaluated by the colour video camera.

5. Method according to claim 4, characterized in that the coated substrate is illuminated on the surface-coated side.

6. Method according to claim 4, characterized in that the coated substrate is illuminated on the side opposite the surface coating.

7. Method according to claim 1, characterized in that the coated substrate is illuminated with diffuse light and in that the light reflected by the surface coating is directly acquired and evaluated by the colour video camera.

8. Method according to claim 7, characterized in that the detection and evaluation by the colour video camera of the light reflected by the surface coating is carried out on a light-absorbing background, preferably a black background.

9. Method according to claim 1, characterized in that, before the determination of the relative colour fractions, the luminance value signals of each pixel in each of the primary colours are subjected to an intensity transformation with a view to optimum exploitation of the colour contrast.

10. Method according to claim 9, characterized in that the intensity transformation of the luminance signals takes place directly using the video signal of the camera, before storage of the signals in the image processing system.

11. Method according to claim 9 or 10, characterized in that, as the intensity transformation, a linear transformation of the intensity interval, between the highest luminosity value and the lowest value measured, onto the entire available intensity range in the image memory is carried out.

12. Method according to claim 9 or 10, characterized in that the known method termed "histogram equation" is used as the intensity transformation.

13. Method according to claim 1, characterized in that the signals delivered by the color video camera or by the image processing stage placed after it, or the signals optimized by the intensity transformation for the luminance in each primary color are subjected to position-dependent two-dimensional filtering before the determination of the relative color fractions.

14. Method according to claim 1, characterized in that, in the case of the evaluation of an extended substrate, for example a coated glass plate after coating in a continuous coating installation, the coated surface is observed simultaneously using a plurality of video cameras, which are each assigned to a partial zone of the coated surface.

15. Method according to claim 1, characterized in that a zone of the coated substrate, in the form of a band extending over the width of the substrate, is acquired and evaluated.

16. Method for the recognition and evaluation of locally limited defects in a surface coating on a substrate by digital data processing of an image delivered by a video camera, characterized in that the coated substrate is illuminated with wide-band light in the visible spectral range, preferably with white light, and a colour video camera is used as the video camera and in that the digital data processing is carried out by detecting, for each pixel, the luminance values for each of the three primary colours and by determining, by dividing the luminance values of each primary colour by the sum of the luminance values of the three primary colours, the relative colour fraction for each primary colour in each pixel, then by comparing the relative colour fractions with predetermined set values, characterized in that the coated substrate is illuminated by light directed at an oblique angle of incidence, in that the light reflected by the surface coating is displayed on a projection screen and in that the diffusely reflected image appearing on the projection screen is acquired and evaluated by the color video camera.

17. Method according to claim 16, characterized in that the coated substrate is illuminated at an angle of incidence of from 0° to 70°, and preferably 20° to 60°.

18. Method according to claim 16 or 17, characterized in that an opaque screen is used as the projection screen.

19. Method according to claim 16 or 17, characterized in that a translucent matt plate is used as the projection screen and the image visible on the matt plate is acquired and evaluated as a transmission image.

* * * * *